United States Patent [19]

Benner et al.

[11] Patent Number: 5,298,404
[45] Date of Patent: Mar. 29, 1994

[54] METHOD FOR PRODUCING THE HPA I RESTRICTION ENDONUCLEASE AND METHYLASE

[75] Inventors: Jack S. Benner, Hamilton, Mass.; Phyllis Rees, Tallahasee, Fla.

[73] Assignee: New England Biolabs, Inc., Beverly, Mass.

[21] Appl. No.: 421,272

[22] Filed: Oct. 13, 1989

[51] Int. Cl.$^5$ .................. C12N 9/22; C12N 15/55
[52] U.S. Cl. .................. 435/199; 435/193; 435/252.33; 435/320.1; 536/23.2
[58] Field of Search .................. 435/172.3, 193, 199, 435/252, 33, 320.1; 536/27, 23.2; 935/29, 73, 80, 82

[56] References Cited

U.S. PATENT DOCUMENTS

| | | | |
|---|---|---|---|
| 4,983,522 | 1/1991 | Barsonian et al. | 435/172.3 |
| 4,983,542 | 1/1991 | Van Cott et al. | 435/172.3 |
| 4,987,074 | 1/1991 | Lannen et al. | 435/172.3 |
| 4,988,620 | 1/1991 | Van Cott et al. | 435/194 |
| 4,996,151 | 2/1991 | Brooks et al. | 435/172.3 |
| 4,999,293 | 3/1991 | Barsonian et al. | 435/172.3 |
| 4,999,294 | 3/1991 | Looney et al. | 435/172.3 |
| 5,002,882 | 3/1991 | Lennen et al. | 435/172.3 |
| 5,004,641 | 4/1991 | Chen et al. | 435/172.3 |
| 5,015,581 | 5/1991 | Benner et al. | 435/172.3 |
| 5,030,569 | 7/1991 | Lunnen et al. | 435/172.3 |

FOREIGN PATENT DOCUMENTS

| | | |
|---|---|---|
| 0193413 | 3/1986 | European Pat. Off. |
| 0248678 | 9/1987 | European Pat. Off. |

OTHER PUBLICATIONS

Greene, P. T., et al. (1981) J. Biol. Chem. 256, 2143-2153.
Walder, R. Y., et al., (1984) J. Biol. Chem. 259, 8015-8026.
Schoner, B., et al. (1983) Gene 24, 227-236.
Newman, A. K., et al. (1981) J. Biol. Chem. 256, 2131-2139.
Suggs, S. V. et al. (1981) Proc. Natl. Acad. Sci., USA 78(11), 6613-6617.
Mann, et al., Gene 3, 97-112 (1978).
Kosykh, et al., Molec. Gen. Genet. 178, 717-719 (1980).
Walder, et al., Proc. Natl. Acad. Sci. USA 78, 1503-1507 (1981).
Bouguelert, et al., Nucleic Acids Res. 12, 3659-3676 (1984).
Gingeras and Brooks, Proc. Natl. Acad. Sci. USA 80, 402-406 (1983).
Theriault and Roy, Gene 19, 355-359 (1982).
Blumenthal et al., J. Bacterol. 164, 501-509 (1985).
Kiss, et al., Nucleic Acids Res. 13, 6403-6421 (1985).
Szomolanyi, et al., Gene 10, 219-225 (1980).
Janulaitis, et al., Gene 20, 197-204 (1982).
Kiss and Baldauf, Gene 21, 111-119 (1983).
Walder, et al., J. Biol. Chem. 258, 1235-1241 (1983).
Lunnen, et al., Gene 74, 25-32 (1988).
Wilson, Gene 74, 281-285 (1988).
Raleigh and Wilson, Proc. Natl. Acad. Sci. USA 83, 9070-9074 (1987).
Heitman and Model, J. Bacteriol. 196 3243-3250 (1987).
Raleigh, et al., Genetics 122, 279-296 (1989).
Hines, et al., Methods in Enzymol. 65, 153-163 (1960).
Brooks, et al., Nucleic Acids Res. 17, 979-997 (1989).
Birnboim and Doly, Nucleic Acids Res. 7, 1513 (1979).
Wilson, Trends in Genetics 4, 314-318 (1988).

*Primary Examiner*—Charles L. Patterson, Jr.
*Attorney, Agent, or Firm*—David G. Conlin; Gregory D. Williams; David S. Resnick

[57] ABSTRACT

The present invention is directed to a method for cloning and producing the Hpa I restriction endonuclease by 1) introducing the restriction endonuclease gene from *Haemophilus parainfluenzae* into a host whereby the restriction gene is expressed; 2) fermenting the host which contains the vector encoding and expressing the Hpa I restriction endonuclease, and 3) purifying the Hpa I restriction endonuclease from the fermented host which contains the vector encoding and expressing the Hpa I restriction endonuclease activity.

7 Claims, 6 Drawing Sheets

HpaI genomic DNA was digested
with KpnI pBIIH1.2KI was digested
with KpnI and dephosphorylated Mixed, ligated at 16°C for 24 hours and
plated on media containing ampicillin Scraped cells to make a primary CsCl-purified plasmid
library, selected library with HpaI endonuclease and plated
selected library on media containing ampicillin Picked 600 colonies in groups of 96, plated
on media containing ampicillin and ampicillin
and streptomycin, over 90% were strepS,
scraped the colonies in groups of 96 and
miniprepped the plasmid DNA Probed the groups of 96 via Southern hybridization using a
HindIII fragment known to contain the HpaI methylase and
the amino terminal end of the HpaI endonuclease.

One plate had the correct sized KpnI
fragment, upon assaying for endonuclease
activity this plate of 96 clones had HpaI
endonuclease activity Colonies were scraped off in groups of eight
Upon assaying for endonuclease activity one group
was positive Grew 10.0ml cultures of these 8 colonies,
miniprepped and looked for resistance to
digestion by HpaI One clone was resistant to HpaI endonuclease activity
Upon assaying for endonuclease activity, this clone
had detectable endonuclease activity and was determined
to have an activity of 40,000 units per gram wet weight
of cells

FIG. I

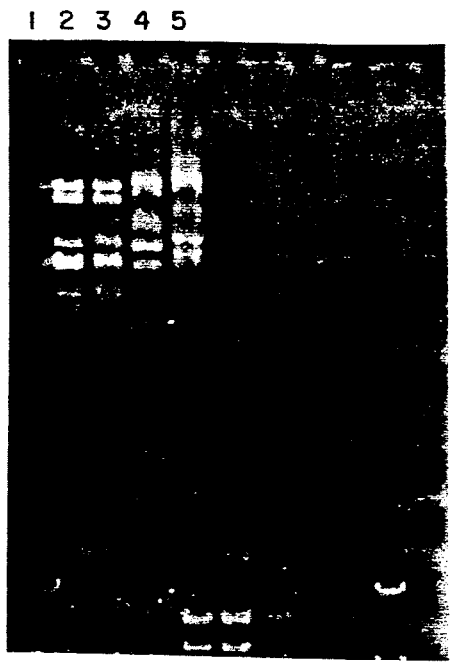

The digests shown above are 1 μg of λ DNA in 50 μl of restriction buffer (10mM Tris-HCl (pH7.5), 10mM MgCl2, .1M NaCl, 100μg/ml BSA) incubated for 15 minutes at 37°C with an additional component listed below for each reaction of interest:

Lane 2   1μl Purified HpaI Endonuclease from *Haemophilus parainfluenzae* cells

Lane 3   1 μl of a cell extract from *E. coli* strain RR1 containing p(pBIIH1.2KI)HpaIRM-10.5-45

Lane 4   5 μl of a cell extract from *E. coli* strain RR1 containing p(pBIIH1.2KI)HpaIRM-10.5-45

Lane 5   10 μl of a cell extract from *E. coli* strain RR1 containing p(pBIIH1.2KI)HpaIRM-10.5-45

FIG. 4

Efficiency of Preparation of Libraries in Relation to Cloning the *Hpa*I Methylase and *Hpa*I Restriction-Modification System Cloning the *Hpa*I Methylase

| Library | Size of Library (# of Transformants) | # of Methylase Clones / # of Clones Screened |
|---------|--------------------------------------|---------------------------------------------|
| *Hind*III | >8000 Colonies | 6/8 |
| *Eco*RI | >8000 Colonies | 0/8 |
| *Bam*HI | >8000 Colonies | 0/8 |
| *Cla*I | >8000 Colonies | 0/8 |
| *Bgl*II | >8000 Colonies | 0/8 |

Cloning the *Hpa*I Restriction-Modification System

| | | |
|---|---|---|
| *Kpn*I | >8000 Colonies | 1/95 |

FIG. 5

*Hpa*I Restriction-Modification Clones p(pBllH1.2Kl)*Hpa*IRM-10.5-45

This clone consists of a 5.5kb *Kpn*I fragment from *H. paraninfluenzae* inserted into the *Kpn*I site of pBllH1.2Kl.

The genes for the *Hpa*I endonuclease and methylase are contained on this 5.5kb *Kpn*I fragment.

Production of *Hpa*I endonuclease = 40,000 Units/gm wet cell paste.

p(pBllH1.2)*Hpa*IRM-7.4-13

This clone consists of a 2.4kb *Eco*RI fragment from *H. paraninfluenzae* inserted into the *Eco*RI site of pBllH1.2.

The genes for the *Hpa*I endonuclease and methylase are contained on this 2.4 kb *Eco*RI fragment.

Production of *Hpa*I endonuclease = 155,000 Units/gm wet cell paste.

p(pBllH1.2)*Hpa*IRM-7.4-2

This clone contains the same *Eco*RI fragment as p(pBllH1.2)*Hpa*IRM-7.4-13 in pBllH1.2, but in the opposite orientation.

Production of *Hpa*I endonuclease = 10,000 Units/gm well cell paste.

FIG. 6

METHOD FOR PRODUCING THE HPA I RESTRICTION ENDONUCLEASE AND METHYLASE

BACKGROUND OF THE INVENTION

The present invention relates to recombinant DNA which encodes the Hpa I restriction endonuclease and modification methylase, and to the production of these enzymes from the recombinant DNA.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., *Gene* 3: 97–112, (1978); EcoRII: Kosykh et al., *Molec. Gen. Genet* 178: 717–719, (1980); PstI: Walder et al., *Proc. Nat. Acad. Sci. USA* 78 1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucleic Acids Res.* 12:3659–3676, (1984); PaeR7: Gingeras and Brooks, *Proc. Natl. Acad. Sci. USA* 80:402–406, (1983); Theriault and Roy, *Gene* 19:355–359, (1982); PvuII: Blumenthal et al., *J. Bacteriol.* 164:501–509, (1985)).

A third approach, and one that is being used to clone a growing number of systems, involves selecting for an active methylase gene (see, e.g. EPO Publication No. 193, 413, published Sept. 3, 1986 and BsuRI: Kiss et al., *Nucleic Acids Res.* 13:6403–6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219–225, (1980); BcnI: Janulaitis et al, *Gene* 20: 197–204 (1982); BsuRI: *Kiss and Baldauf, Gene* 21: 111–119, (1983); and MspI: Walder et al., *J. Biol. Chem.* 258:1235–1241, (1983)). For an overall review of cloning restriction-modification systems, see e.g., Lunnen et al., *Gene* 74:25–32 (1988) and Wilson G.G., *Gene* 74:281–285 (1988).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070-9074, (1986)) or methylated adenine (Heitman and Model, *J. Bact.*, 196:3243-3250, (1987); Raleigh, Trimarchi, and Revel, *Genetics*, 122:279-296, (1989)). Cytosine-specific or adenine-specific methylase genes cannot be cloned easily into these strains, either on their own, or together with their corresponding endonuclease genes. To avoid this problem it is necessary to use mutant strains of *E. coli* (McrA⁻ and McrB⁻ or Mrr⁻) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to obtainable recombinant DNA including the gene for the Hpa I restriction endonuclease and modification methylase from *Haemophilus parainfluenzae* (NEB strain #127, a sample of which was deposited in the ATCC under designation number #53913), as well as to related methods for production of these enzymes from the recombinant DNA. This invention also relates to a transformed host which expresses the restriction endonuclease Hpa I, an enzyme which recognizes the DNA sequence GTT▼AAC and cleaves as indicated between the second 5' T and first 5' A by the arrow. See Hines, J. L., Chauncey, T. R., and Agarwal, K. L., *Methods in Enzymology*, 65:153-163, (1960), the disclosure of which is hereby incorporated by reference herein.

The preferred method for cloning Hpa I comprises forming a sufficient number of libraries containing DNA from *Haemophilus parainfluenzae*, selecting those clones which express the corresponding methylase gene by incubating the library DNA with an appropriate restriction endonuclease, i.e. an enzyme that cleaves its recognition sequence when it is not methylated; and retransforming a host with recombinant DNA which has not been cleaved by being incubated with the restriction endonuclease and screening the resulting transformants for positive clones among survivors.

BRIEF DESCRIPTION OF THE DRAWINGS

FIG. 1 illustrates the scheme for cloning the Hpa I restriction endonuclease.

FIG. 4 is a photograph of an agarose gel demonstrating Hpa I restriction endonuclease activity in cell extracts of *E. coli* RR1 (ATCC 31343) carrying p(pBIIHI.2KI)HpaIRM-10.5-45.

FIG. 5 is a table of the numbers of transformants obtained for each library prepared, the number of Hpa I methylase clones or Hpa I restriction-modification clones obtained from each library.

FIG. 6 is a list of the Hpa I restriction-modification clones described in this patent.

DETAILED DESCRIPTION OF THE INVENTION

Figure 2:
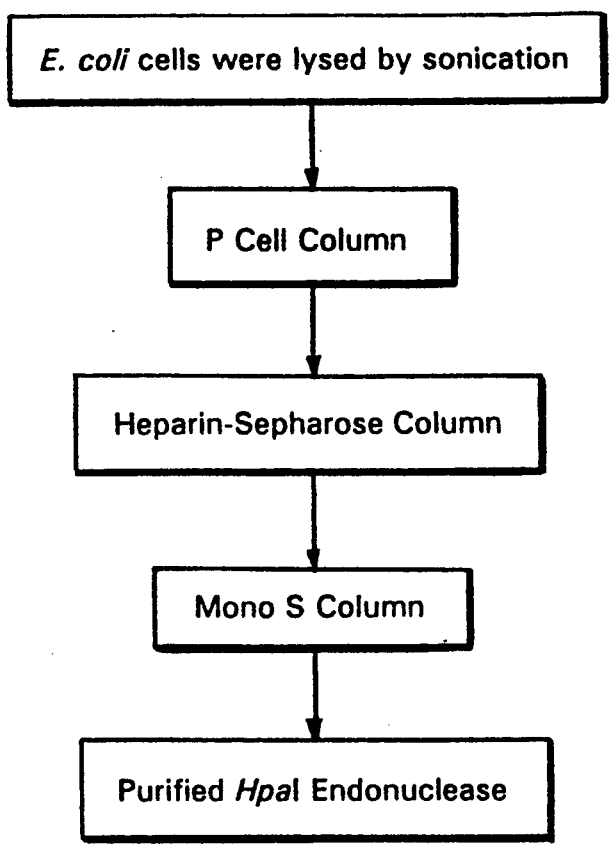
FIG. 2 illustrates the scheme for producing the Hpa I restriction endonuclease.

The present invention relates to recombinant DNA which encodes the Hpa I restriction endonuclease and modification methylase, as well as to the enzymes produced from such a recombinant DNA.

The method described herein by which the Hpa I restriction gene and methylase gene are preferably cloned and expressed is illustrated in FIG. 1 and includes the following steps:

I. CLONING THE HPA I METHYLASE

A. Preparation of Libraries

A-1. *Haemophilus parainfluenzae* is grown in accordance with the standard protocols for growing Haemophilus species at New England Biolabs, and the cells are lysed and the genomic DNA purified by the techniques described in Brooks, et al., *Nucleic Acids Research*, 17:979-997, (1989), and is described in detail in the example.

A-2. The genomic DNA is digested fully with the following restriction endonucleases: Hind III, EcoR I, Bgl II, BamH I, and Cla I.

A-3. These restriction enzyme fragments are ligated into a corresponding cloning site (i.e. Hind III generated fragments are ligated into the Hind III cloning site, and so on) of a cloning vector, ideally one that has one, two or three Hpa I sites and the cloning site, such as pBIIHI.2 (ATCC 67902),or pBIIHI.2KI or pACYC177 (ATCC 37031) and the mixture is used to transform an appropriate host cell such as *E. coli* RR1 cells which are mrr⁻ or any other *E. Coli* strain which is mrr⁻ and/or McrA⁻.

A-4. The transformed mixture is plated onto media selective for transformed cells, such as the antibiotics ampicillin, tetracycline, or chloramphenicol. After incubation, the transformed colonies are collected together into a single culture, the cell library.

A-5. The recombinant plasmids are purified in toto from the cell library to make the plasmid library.

B. Selection and Screening of the Libraries

B-1. The plasmid library is digested to completion in vitro with the Hpa I restriction endonuclease, prepared from *Haemophilus parainfluenzae*, by a method similar to that described in Watson et al, supra. Hpa I digestion differentially destroys unmodified, non-methylase-containing, clones, increasing the relative frequency of Hpa I methylase clones.

B-2. The selected DNA is transformed back into an appropriate host such as *E. coli* RR1, and transformants are recovered by plating onto selective media. The colonies are picked and their DNA is analyzed for the presence of the Hpa I modification gene: the plasmids that they carry are purified and incubated with the Hpa I restriction endonuclease to determine whether they are resistant to digestion. Total cellular DNA (chromosomal and plasmid) is also purified and incubated with the Hpa I restriction endonuclease. The DNA of clones that carry the Hpa I modification gene should be fully modified, and both plasmid DNA and total DNA should be substantially resistant to digestion.

C. Preparation of Hpa I Endonuclease Protein, Protein Sequencing the Hpa I Endonuclease, Mapping the Location of the Endonuclease C-1. The Hpa I restriction endonuclease is produced from *Haemophilus parainfluenzae* cells carrying the Hpa I restriction and modification genes. The cells are propagated in a fermenter in a rich medium. The cells are harvested by centrifugation. The cells are disrupted by a gaulin mill to produce crude cell extract containing the Hpa I restriction endonuclease activity. The crude cell extract containing the Hpa I restriction endonuclease activity is purified by standard ion-exchange and affinity chromatography techniques.

C-2. The endonuclease so purified is homogeneous on SDS polyacrylamide gel electrophoresis and has a molecular weight of 30,000 daltons and a specific activity of approximately 250,000 units/mg of protein titered on lambda DNA.

C-3. The amino terminal sequence of the endonuclease is obtained using an Applied Biosystems 470A Protein Sequencer (Brooks, et al., *Nucleic Acids Research*, 17:979–997, (1989)), and a DNA oligonucleotide probe is made based on the protein sequence.

C-4. The probe is used to map the location of the endonuclease on the methylase clone as well as to the *Haemophilus parainfluenzae* genome.

II. CLONING THE HPA I RESTRICTION-MODIFICATION SYSTEM

A. Preparation of the Library

A-1. *Haemophilus parainfluenzae* genomic DNA, prepared as described in I (A-1), is digested fully with a restriction endonuclease such as Kpn I restriction endonuclease.

A-2. The resulting Kpn I fragments are ligated into the Kpn I cloning site of a cloning vector, which has ideally one, two or three Hpa I sites and a Kpn I cloning site, such as pBIIHI.2KI, and the mixture is used to transform an appropriate host cell such as *E. coli* RR1 cells.

A-3. The transformed mixture is plated onto media selective for transformed cells, such as the antibiotics ampicillin, streptomycin, or chloramphenicol. After incubation, the transformed colonies are collected together into a single culture, the cell library.

A-4. The recombinant plasmids are purified in toto from the cell library to make the plasmid library.

B. Selection and Screening of the Library

B-1. The plasmid library is digested to completion with the Hpa I restriction endonuclease, prepared from *Haemophilus parainfluenzae*, by a method similar to that described in Watson et al, supra. Hpa I digestion differentially destroys unmodified, non-methylase-containing, clones, increasing the relative frequency of Hpa I methylase clones.

B-2. The selected DNA is transformed back into an appropriate host such as *E. coli* RR1, and transformants are recovered by plating onto selective media. The colonies are picked and their DNA is analyzed for the presence of the Hpa I modification gene: the plasmids that they carry are purified and incubated with the Hpa I restriction endonuclease to determine whether they are resistant to digestion. Total cellular DNA (chromosomal and plasmid) is also purified and incubated with the Hpa I restriction endonuclease. The DNA of clones that carry the Hpa I modification gene should be fully modified, and both plasmid DNA and total DNA should be substantially resistant to digestion.

B-3. Clones carrying the Hpa I restriction endonuclease are identified by preparing crude extracts of the clones which were determined to carry the Hpa I methylase gene, and assaying the crude extract for Hpa I restriction endonuclease activity. The level of Hpa I activity in the crude cell extract is determined.

C. Restriction Mapping the Hpa I Restriction-Modification Clone and Preparation of Deletion Subclones C-1. A number of restriction endonuclease sites are mapped on clones identified as containing the Hpa I restriction endonuclease and modification methylase and the positions of the genes have been determined by deletion subcloning and mapping via Southern hybridizations using DNA oligomers as probes.

C-2. Various subclones are prepared in an attempt to make a clone that produces more Hpa I endonuclease.

C-3. The Hpa I restriction endonuclease is produced from cells carrying the Hpa I restriction and modification genes. The cells are propagated in a fermenter in a rich medium containing ampicillin. The cells are harvested by centrifugation. The cells are disrupted by sonication to produce crude cell extract containing the Hpa I restriction endonuclease activity. The crude cell extract containing the Hpa I restriction endonuclease activity is purified by standard ion-exchange and affinity chromatography techniques.

C-4. The endonuclease so purified is found to be homogeneous on SDS polyacrylmide gel electrophoresis and to have a molecular weight of 30,000 daltons and a specific activity of approximately 250,000 units/mg of protein titered on lambda DNA.

Although the above-outlined steps represent the preferred mode for practicing the present invention, it will be apparent to those skilled in the art that the above-described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Hpa I Restriction Endonuclease Gene

I. CLONING THE HPA I METHYLASE

A. Preparation of Libraries

A-1. Genomic DNA purification; Approximately five grams of *Haemophilus parainfluenzae* cells were thawed and resuspended in 0.1M Tris-HCl, pH 7.1, 0.1M ETDA (25 ml) in a Corning plastic tube (50 ml). A solution of 60 mg of lysozyme in 35 ml of the above buffer was divided into two 50 ml plastic tubes and equal portions (15 ml) of the cell suspension added to each. The solutions were incubated at 37° C. for fifteen minutes. SDS was added from a 20% stock solution to adjust the final concentration of SDS to 1%. 200 ul of a Proteinase K (20 mg/ml stock) was added and incubated for one hour at 37° C. The solution appeared stringy and diffuse at this point but was not clear. Added 2 ml of 10% SDS/8% sarcosyl to the tubes (1 ml each) and heated at 55° C. for two hours. The sample remained stringy but not totally cleared. The samples were dialyzed against TE (10 mM Tris-HCl, pH 7.1, 1 mM EDTA) (2 l) with a single change—total 16 hours. After the dialysis the solution (98 ml) was prepared for CsCl gradients by dilution with an equal vol. of TE pH 8.0, divided into two portions and to each an addition of 98.0 g of CsCl and 1 ml of a 5 mg/ml Ethidium bromide was made. The twenty tubes were spun in the Ti70 rotor for 48 hrs at 44,000 rpm. The bands were removed and extracted with CsCl-water-saturated isopropanol. The solution was dialyzed against the same buffer (4 l) as before and then phenol and chloroform extracted (one time each). This solution was dialyzed once again to remove phenol and then subjected to electrophoresis.

A-2. Limit digestion: The purified DNA was cut with Hind III, EcoR I, BamH I, Bgl II, and Cla I to achieve total digestion as follows: 300 ul of DNA at 100 ug/ml in 10 mM Tris pH 7.5, 10 mM MgCl$_2$, 100 mM NaCl, 10 mM mercaptoethanol buffer was dispensed into three tubes. To the tube was added 50 units of Hind III. The tubes were incubated at 37° C. for one hour, then phenol/chloroform extracted and ethanol precipitated. The pellets were redissolved in 300 ul of 10 mM Tris-HCl, 1 mM EDTA, pH 8.0 and 10 ul from each analyzed by agarose gel electrophoresis.

A-3. Ligation: The fragmented DNA was ligated to pBIIHI.2 (pN01523, with a Hpa I linker inserted into the Pvu II site and a Bgl II linker inserted into the EcoR I site) as follows: 10.0 ug of Hind III, EcoR I, BamH I, Bgl II, or Cla I digested *Haemophilus parainfluenzae* DNA (100 ul) was mixed with 2.0 ug of Hind III, EcoR I, BamH I, Bgl II, or Cla I-cleaved and dephosphorylated pBIIHI.2 (20.0 ul) and ethanol precipitated. The DNA was centrifuged at 12,000 g, 4° C. for 15 minutes and washed once with 100 ul 70% ethanol. The DNA was resuspended in 99 ul of 1× ligation buffer (50 mM Tris, pH 7.5, 10 mM MgCl$_2$ 10 mM DTT, 0.5 mM ATP), 1 ul of T4 DNA ligase was added and the mixture allowed to incubate at 16° C. for 16 hours. Aliquots of 2.5 and 5.0 ul were used to transform *E. coli* strain RR1 as follows: Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C.

A-4. Primary Cell Libraries: The transformed cell cultures were centrifuged, resuspended in 250 ul volumes and plated onto Luria-agar (L-agar) plates containing 100 ug/ml ampicillin. After overnight incubation at 37° C., the plates were removed and the approximately 8000 colonies scraped-up into 25 ml of LB with antibiotic. Plasmid DNA was prepared from these cells as follows: the cells were pelleted by centrifugation and three grams of cell paste was resuspended in 14 ml of 25 mM Tris-HCl, 10 mM EDTA pH 8.0 and 50 mM glucose. The suspension was made 4.0 mg/ml in lysozyme and incubated at 25 degrees for 5 minutes. A 27 ml aliquot of 1% sodium dodecyl sulfate and 0.2N NaOH was added followed by mixing of the solution and incubated for 5 minutes at 0 degrees. Genomic DNA was precipitated by the addition of 20 ml of ice-cold 3M potassium acetate, pH 4.8, vortexed gently for 10 seconds, left on ice for 5 minutes and centrifuged at 12,000×g for ten minutes. The supernatant was removed and extracted with an equal volume of phenol/chloroform (1:1). The layers were separated by centrifugation at 10,000×g for 5 minutes. The upper layer was removed and extracted with an equal volume of chloroform. The layers were separated by centrifugation at 10,000 g for 5 minutes. The upper layer was removed and the nucleic acids precipitated by the addition of two volumes of ethanol. The precipitate was collected by centrifugation at 12,000×g for twenty minutes. The pellet was washed with 70% ethanol once and repelleted as before. The pellet was dried under vacuum and resuspended in 8 ml of 10 mM Tris-HCl, 1 mM EDTA, pH 8.0. The DNA solution was prepared for cesium chloride-ethidium bromide equilibrium density centrifugation by the addition of 8.9 grams of cesium chloride and 0.9 ml of a solution of ethidium bromide (5 mg/ml) were added. The DNA solution was centrifuged at 44,000 rpm for 48 hours and the resulting plasmid band of DNA was removed with a syringe and 18 g needle. The ethidium bromide was removed by extracting with an equal volume of CsCl-water-saturated isopropanol. The cesium chloride was removed by dialysis. The DNA was extracted with an equal volume of phenol/chloroform (1:1), and ethanol precipitated. The resultant DNA pellet was resuspended in 1.0 ml 10 mM Tris-HCl, 1 mM EDTA, pH8.0.

B. Selection and Screening of the Libraries

B-1. Primary Selection and Selected Library: 2 ug (30.0 ul) of the Hind III EcoR I, BamH I, Bgl II, and Cla I plasmid libraries were diluted into 60 ul of restriction endonuclease digestion buffer (10 mM Tris pH 7.5, 10 mM MgCl$_2$, 10 mM mercaptoethanol, 100 mM NaCl and 100 ug of bovine serum albumin). 100 units (3 ul) of Hpa I restriction endonuclease were added and the tube was incubated at 37° C. for 2 hr, at which time 7 U (1 ul) of calf intenstinal phosphatase was added and the reaction was incubated for an additional 30 minutes. Aliquots of this reaction mixture, 2 ul and 4 ul, were mixed with 200 ul of ice-cold competent *E. coli* RR1 cells and transformed, plated and grown overnight as for the primary library.

B-2. Analysis of individuals: Colonies from the above transformation were picked and plated on LB agar plates containing ampicillin and LB agar plates containing ampicillin and streptomycin. Eight colonies, from the Hind III library which were amp$^R$ and strep$^S$ were grown up in 10 ml cultures and the plasmids that they carried were prepared by the following miniprep purification procedure, adapted from the method of Birnboim and Doly (Nucleic Acids Res. 7: 1513 (1979)).

Miniprep Procedure: Each culture was processed as follows: The 1.5 ml overnight culture was pelleted at 6,000×g for 5 minutes. The supernatant was poured off and the cell pellet was resuspended in 150 ul of 25 mM Tris, 10 mM EDTA, 50 mM glucose, pH 8.0, containing 1 mg/ml lysozyme. After five minutes at room temperature, 200 ul of 0.2M NaOH, 1% SDS was added and the tube was shaken to lyse the cells, then placed on ice. After five minutes, 150 ul of 3M sodium acetate, pH 4.8, was added and shaken and placed on ice for an additional five minutes. The precipitate that formed was spun down at 12,000×g, 4° C. for 10 minutes. The supernatant was removed and extracted with an equal volume of phenol/chloroform (1:1). The layers were separated by centrifugation at 10,000×g for five minutes. The supernatant was poured into a centrifuge tube containing 880 ul of ethanol and mixed. After 10 minutes at room temperature, the tube was spun at 12,000×g for 10 minutes to pellet the precipitated nucleic acids. The supernatant was discarded and the pellet was washed again with one ml of 70% ethanol-water, repelleted and dried at room temperature for 30 minutes under vacuum. Once dry, the pellet was resuspended in 50 ul of 10 mM Tris, 1 mM EDTA, pH 8.0 containing 20 ug/ml RNase and incubated for 1 hour at 37° C. to digest the RNA.

The plasmid minipreps were subsequently analyzed by digestion with Hpa I and Hind III.

B-3. Methylase Gene Clones: 75% of the plasmids that were analyzed were found to be resistant to Hpa I and to carry a Hind III fragment of approximately 2.3 Kb in length. These plasmids were subsequently shown to carry only the Hpa I modification methylase gene and not the restriction endonuclease gene. The other 25% of the plasmids looked at were not resistant to Hpa I and contained spurious fragments or were vector religated. No clones were found in the other four libraries, EcoR I, BamH I, Bgl II, and Cla I that were resistant to cleavage by Hpa I endonuclease and hence these libraries were not looked at any further.

B-4. Restriction Gene Clones: The clones identified above (section I (B-3)) as carrying the Hpa I modification methylase gene were also tested for the Hpa I restriction endonuclease gene. This was performed as follows: The remaining portion of the overnight culture was used to check for endonuclease activity. This was done as follows:

Endonuclease Assays:

10× restriction endonuclease buffer: 100 mM Tris, pH 7.5, 100 mM $MgCl_2$, 100 mM 2-mercaptoethanol, 1M NaCl.

Cell extracts were prepared as follows: Cells from one ml were pelleted by centrifugation at 4,000 rpm for five minutes. The supernatant was discarded and the pellet was resuspended in one ml of sonication buffer (50 mM Tris, pH 8.0, 5 mM DTT, 5% glycerol) and sonicated gently for two 10-second bursts to disrupt the cells. The tube was spun for ten minutes in a microcentrifuge at 4° C., and the supernatant was used as the cell extract. The extract, 1 ul and 10 ul, were incubated with one ug of lambda DNA in 50 ul of 1× restriction endonuclease buffer for fifteen minutes at 37° C. None of the clones tested had endonuclease activity.

C. Preparation of Hpa I Endonuclease Protein, Protein Sequencing the Hpa I Endonuclease, Mapping the Location of the Hpa I Endonuclease, and DNA Sequencing in the Region of the Hpa I Endonuclease C-1. Hpa I endonuclease from *Haemophilus parainfluenzae* designated NEB# 127 was propagated in a fermenter at 37 degrees C in TRY-YE Broth medium consisting of: tryptone, 10.0 g per liter; yeast extract, 5.0 g per liter; NaCl, 2.0 g per liter; $K_2HPO_4$, 4.4 g per liter; glucose, 2.0 g per liter; hemin bovine, 10 mg per liter; NAD;DPN, 2.0 mg per liter. The cells are collected by centrifugation and the cell paste is used fresh or stored at −70° C.

C-2. All subsequent steps are carried out at 4° C.

C-3. The cell paste (362 grams) is thawed and the cells are resuspended in 1000 ml sonication buffer (50 mM Tris, pH 8.0, 5 mM DTT, 5% glycerol).

C-4. The cells are disrupted by a gaulin mill to achieve release of approximately 50 mg of soluble protein per ml of suspended cells.

C-5. The insoluble cell debris is removed by centrifugation at 15,000×g for 40 minutes.

C-6. The supernatant fluid is subjected to a streptomycin sulfate precipitation (5% weight per volume) as follows:

17.35 grams of streptomycin sulfate was added to 347 mls of sonication buffer, this solution was added, slowly, to the supernatant, at 4° C., over a 45 minute period. The solution was stirred for an additional 30 minutes, centrifuged for 30 minutes at 4° C., 21,000×g and the supernatant collected.

C-7. The supernatant fluid was subjected to an ammonium sulfate precipitation (70%) as follows:

660 grams of ammonium sulfate was added to 1.4 liters of the supernatant over a period of 45 minutes. The solution was stirred for a additional 30 minutes and then centrifuged for 30 minutes, 4° C., 21,000×g and the precipitate collected.

The precipitate was resuspended in 600 ml of a 40% saturated solution of ammonium sulfate solution (made up in the sonication buffer). An additional 97 g of ammonium sulfate was added to bring the solution up to a saturation level of 55%. The solution was stirred for 30 minutes at 4° C. and then centrifuged for 30 minutes at 4° C. and 21,000×g.

The precipitate was collected and resuspended in 300 ml 20 mM $K_2HPO_4$, pH 6.9, 0.1 m MEDTA, 5 mM DTT, 10% glycerol. Dialyzed against the same buffer. Then diluted with 2 volumes of the same buffer.

C-8. The supernatant fluid is applied to a phosphocellulose column (5×35 cm) (Whatman P-11) equilibrated with 20 mM $K_2HPO_4$, pH 6.9, 50 mM NaCl, 5 mM DTT, and 10% glycerol. The column is washed with two column volumes of the above buffer. The flow-though from the column is collected in a single flask. Hpa I endonuclease is retained by the column and elutes between 0.3 and 0.6M NaCl. The most active fractions are pooled and dialyzed against 20 mM $K_2HPO_4$, pH7.4, 0.5 mM EDTA, 5mM DTT, 10% glycerol, and 0.5M KCl.

C-9. The pool from the phosphocellulose column is applied to a Heparin-Sepharose CL-6B column (2.5×25 cm) equilibrated with 20 mM $K_2HPO_4$, pH 7.4, 0.5 mM EDTA, 5 mM DTT, 0.05M KCl, 10% glycerol and washed with two column volumes of the same buffer. A linear gradient of KCl from 0.05M to 1.0M (total volume 700 ml) is developed and applied to the column. Ten ml fractions are collected. The fractions are assayed for the presence of the Hpa I restriction endonuclease activity on lambda DNA. The active fractions are pooled and dialysed against 100 volumes of buffer S (20 mM $K_2HPO_4$, pH6.9 0.1 mM EDTA, 5 mM DTT, 0.05M KCl, 10% glycerol).

C-10. The dialyzed pool (50 ml) of Hpa I activity is applied to a 1 ml Mono S FPLC column (Pharmacia) and washed with buffer S (20 mM $K_2PO_4$, pH 6.9, 5 mM DTT, 10% glycerol, 0.05 M KCl, 0.1 mM EDTA) and a 40 ml linear gradient from 50 mM KCl to 1.0M KCl is developed in S buffer and applied to the column. One ml fractions are collected and assayed for the presence of Hpa I restriction endonuclease activity. The four most active fractions were homogeneous and were found to have a specific activity of approximately 250,000 units/mg protein and a molecular weight on SDS-polyacrylamide gels of 30,000 Daltons.

C-11. 10 ug of the homogeneous Hpa I endonuclease was subjected to amino terminal protein sequencing on an Applied Biosystems Model 470A gas phase protein sequencer (Brooks, et al., Nucleic Acids Research, 17:979-997, (1989)). The first 20 residues were degraded. The sequence of the first 11 residues obtained was the following: X K V/Y E E I N F K V/Y P (refer to Table 1 for explanation of 1 letter code for protein sequence).

Figure 3:
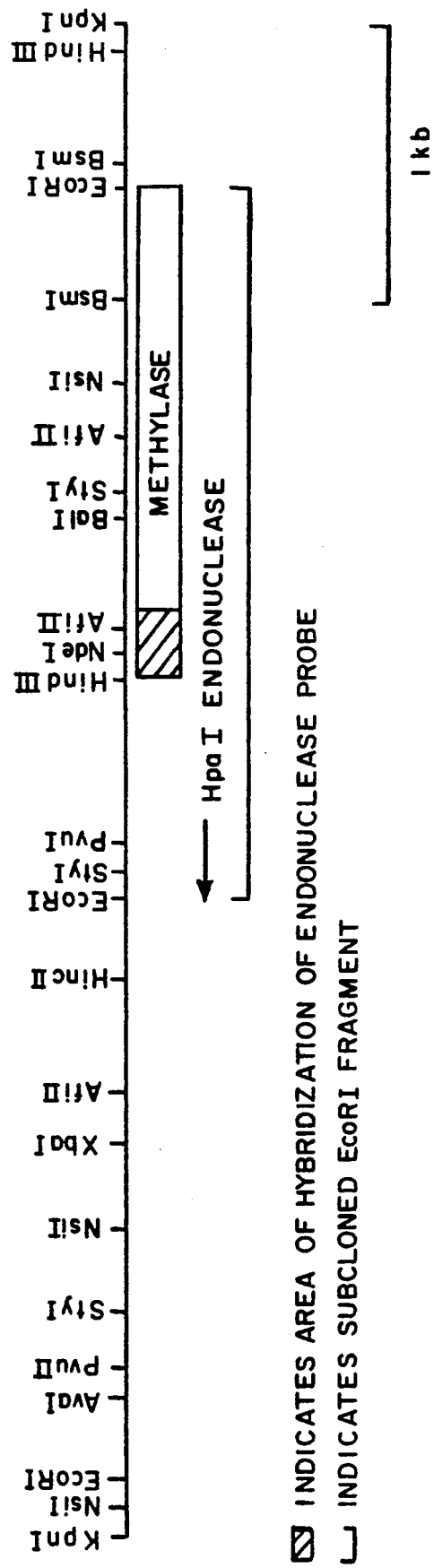
FIG. 3 is a restriction map of the 5.5 Kb Kpn I fragment from *Haemophilus parainfluenzae* that encodes the Hpa I restriction endonuclease and modification methylase. The fragment was cloned into the Kpn I site of pBIIHI.2KI (NEB #560. a sample of which has been deposited at the ATCC under designation number 68002) to create p(pBIIHI.2KI)HpaIRM-10.5-45 a sample of which has been deposited at the ATCC on Dec. 4, 1991 under ATCC Accession No. 75169.

C-12. Based on the protein sequence, a 17-mer was made with the following sequence: 5' TT CCA RTT DAT YTC YTC 3' (Y=T, C; D=A, G, T; R=A or G) which was used to map the location of the amino terminal end of the endonuclease on p(pBIIHI.2)HpaIM7.5-A10. DNA sequence was obtained, which in conjunction with the probe hybridization results, determined the direction of the endonuclease. The DNA sequence obtained was the following:5' AAG CTT TAG TCG AAT TAG AAC TGC ATA TGT TAA AGA CCC TAA TTT TAT TTT TAT AAT ATT ATC CAT AAA ACA CAG TGT ATA TGT AAA AAG AAA TGA ATA CAC AAA TTT AAT GGA TGG AAT AAT GCA AAT TAT TGA CTT TAA TGT TTA TGA TTT AAA GTA TAT ATC TGA TTC AGA CAT AAG TTA TAA CCC AGC ATT AG 3'. The 17-mer oligomer and the methylase clone obtained from the Hind III library (p(pBIIHI.2)HpaIM-7.5-A10) were used to map the endonuclease gene and methylase gene to various restriction fragments of the *Haemophilus parainfluenzae* genome. See FIG. 3 for a restriction map of p(pBIIHI.2)HpaIM10.5-A10 and for the location of where the endonuclease probe hybridized on the methylase clone.

II. CLONING THE HPA I RESTRICTION-MODIFICATION SYSTEM

A. Preparation of the Library

A-1. Based on the data obtained in I (C-11), purified *Haemophilus parainfluenzae* genomic DNA (prepared as in I (A-1)) was subjected to a limit digestion using Kpn I as follows: 300 ul of DNA at 100 ug/ml in 10 mM Tris pH 7.5, 10 mM MgCl$_2$, 0 mM NaCl, 10 mM mercaptoethanol buffer was dispensed into one tube. To the tube was added 50 units of Kpn I. The tubes were incubated at 37° C. for one hour, then phenol/chloroform extracted and ethanol precipitated. The pellets were redissolved in 300 ul of 10 mM Tris-HCl, 1 mM EDTA, pH 8.0 and 10 ul from each analyzed by agarose gel electrophoresis.

A-2. Ligation: The fragmented DNA was ligated to pBIIHI.2KI (pN01523, with a Hpa I linker inserted into the Pvu II site, a Bgl II linker inserted into the EcoR I site and a Kpn I linker inserted into the EcoR V site) as follows: 10.0 ug of Kpn I digested *Haemophilus parainfluenzae* DNA (100 ul) was mixed with 2.0 ug of Kpn I-cleaved and dephosphorylated pBIIHI.2KI (20.0 ul) and ethanol precipitated. The DNA was centrifuged at 12,000 g, 4° C. for 15 minutes and washed once with 100 ul 70% ethanol. The DNA was resuspended in 99 ul of 1× ligation buffer (50 mM Tris, pH 7.5, 10 mM MgCl$_2$ 10 mM DTT, 0.5 mM ATP), 1 ul of T4 DNA ligase was added and the mixture allowed to incubate at 16° C. for 16 hours. Aliquots of 2.5 and 5.0 ul were used to transform *E. coli* strain RR1 as follows: Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C.

A-3. Primary Cell Library: Prepared as in step I (A-4) with one additional step: based on the data obtained from step I (C-10), the libraries were probed (via Southern hybridization) with the Hind III fragment (isolated from p(pBIIHI.2)HpaIM-7.5-A10) containing the entire Hpa I methylase and the amino terminal end of the endonuclease, looking for a Kpn I fragment of the appropriate size which was presumed to contain the endonuclease and methylase. This fragment was present in the primary cell library.

B. Selection and Screening of the Library

B-1. Primary Selection and Selected Library: Prepared as in step I (B-1). The selected library was probed as described in step II (A-2).

B-2. Analysis of individuals: Colonies from the above transformation were picked and plated on LB agar plates containing ampicillin and LB agar plates containing ampicillin and streptomycin. Approximately 90% were streptomycin$^S$.

B-3. The colonies were scraped off the plates in groups of 96 using LB containing 100 ug/ml ampicillin and miniprepped in the following manner:

The cell pellet was resuspended in 2.0 ml of 25 mM Tris, 10 mM EDTA, 50 mM glucose, pH 8.0, containing 1 mg/ml lysozyme. After five minutes at room temperature, 4.0 ml of 0.2M NaOH, 1% SDS was added and the tube was shaken to lyse the cells, then placed on ice. After five minutes, 3.0 ml of 3M sodium acetate, pH 4.8, was added and shaken and placed on ice for an additional five minutes. The precipitate that formed was spun down at 12,000×g, 4° C. for 10 minutes. The supernatant was removed and extracted with an equal volume of phenol/chloroform (1:1). The layers were separated by centrifugation at 10,000×g for five minutes. The supernatant was removed and extracted with an equal volume of chloroform (1:1). The layers were separated by centrifugation at 10,000×g for five minutes. The supernatant was poured into a centrifuge tube containing 18.0 ml of ethanol and mixed. After 2 minutes at room temperature, the tube was spun at 12,000×g for 20 minutes to pellet the precipitated nucleic acids. The supernatant was discarded and the pellet was washed again with five ml of 70% ethanol-water, repelleted and dried at room temperature for 30 minutes under vacuum. Once dry, the pellet was resuspended in 500 ul of 10 mM Tris, 1 mM EDTA, pH 8.0 containing 20 ug/ml RNase and incubated for 1 hour at 37° C. to digest the RNA.

B-4. The plasmid DNA from the plate scrapes of step II (B-3) was probed with the Hind III fragment containing the methylase gene (see step II (A-3)) and one plate was found to contain the correct-sized Kpn I fragment.

B-5. Colonies were scraped off in groups of eight from the 'positive' plate (see section II (B-4)) and assayed for endonuclease activity as per step I (B-4). One group of eight had Hpa I activity.

B-6. Eight colonies (see section II (B-5)) were miniprepped (see section I (B-2)) and one was found to have the correct sized Kpn I fragment, and to be resistant to digestion by Hpa I endonuclease.

B-7. Restriction Gene Clones: The clone identified above (section II (B-6)) as carrying the Hpa I modification methylase gene was also tested for the Hpa I restriction endonuclease gene. This was performed as described in section B4. This clone was found to have Hpa I endonuclease activity and to synthesize about 40,000 units of Hpa I restriction endonuclease per gram of wet cell paste.

C. Restriction Mapping the Hpa I Restriction-Modification Clone and Preparation of Deletion Subclones C-1. p(pBIIHI.2KI)HpaIRM-10.5-45 was used to transform an isogenic series of *E. coli* strains, looking for potential effects caused by either the Mcr A, Mcr B or mrr phenotypes. It was discovered that this RM clone was unable to transform, and hence be propagated, in any mrr+ strains.

C-2. Hpa I endonuclease was prepared from *E. coli* RRI cells containing p(pBIIHI.2KI)HpaIRM10.5-45 as described in section I, parts C1-C10 with a few alterations: the cells were grown in LB Broth medium consisting of 10 grams per liter, casein hydrolysate; 5 grams per liter, yeast extract; 10 grams per liter, NaCl; 1 gram per liter, magnesium chloride-hexahydrate; 1 gram per liter, glucose; 100 mg per liter ampicillin, the pH is adjusted to 7.2 with NaOH; the cells were lysed by sonication; the streptomycin sulfate and ammonium sulfate precipitation steps were not performed. The endonuclease purified was found to produce 40,000 units of Hpa I endonuclease per gram of cells and to have a specific activity of approximately 250,000 units/mg protein.

C-3. 30 ug of p(pBIIHI.2KI)HpaIRM10.5-45 were digested with EcoR I restriction endonuclease as follows: 300 ul of DNA at a concentration of 100 ug/1 ml in 10 mM Tris, pH7.5, 10 mM MgCl$_2$, 100 mM NaCl, 10 mM mercaptoethanol was dispensed in one tube. To the tube was added 100 units of EcoR I endonuclease and the reaction was incubated for 2 hours at 37° C. The whole digest was run out on a 0.7% agarose preparative gel. The fragment of choice, an approximately 2.3 kb EcoR I fragment, determined to contain the whole methylase gene and thought to contain the whole endonuclease gene, was cut out of the gel. The gel fragment was alternately extruded through a 21 gauge needle and frozen. This was repeated three times. The resultant mixture was centrifuged at 100,000×g for 1 hour at 4° C. to pellet the agarose. The aqueous solution remaining was brought up to a NaCl concentration of 0.4M and precipitated with 2 volumes of isopropanol. The DNA was pelleted by centrifugation at 12,000×g for 20 minutes and washed once with cold 70% ethanol. The DNA pellet was resuspended in 2 ml TE and extracted with an equal volume of phenol. The layers were separated by centrifugation at 10,000×g for 10 minutes. The upper layer was removed and extracted with an equal volume of phenol/chloroform (1:1), and the layers were separated by centrifugation at 10,000×g for 10 minutes. The upper layer was removed and extracted with an equal volume of chloroform and centrifuged at 10,000×g to separate the layers. The aqueous layer was removed, and the DNA precipitated by the addition of 1/10 volume (0.2 ml) 2.75M sodium acetate and 2 volumes of cold ethanol. The DNA was pelleted by centrifuging at 12,000×g for 20 minutes and washed once with cold 70% ethanol. The DNA was resuspended in 0.5 ml TE.

C-4. The gel prepped EcoR I fragment was ligated into the EcoR I site of pBIIHI.2 in the following manner: 60 ul of the gel prepped EcoR I fragment (0.5 ug) was mixed with 5 ul of EcoR I cut and dephosphorylated pBIIHI.2 (0.5 ug) To this was added 1/10 volume (10 ul) sodium acetate, 35 ul TE and 2 volumes cold ethanol (200 ul). The DNA was pelleted by centrifugation at 12,000×g, 4° C. for 15 minutes and washed once with 100 ul 70% ethanol. The DNA was resuspended in 20 ul of 1× ligation buffer (50 mM Tris, pH7.5, 10 mM MgCl$_2$, 10 mM DTT, 0.5 mM ATP) and 1 ul of T4 DNA Ligase was added and the mixture was allowed to incubate at 16° C. for 16 hours. Aliquots of 1, 2, and 3 ul were used to transform *E. coli* strain RRI as described in section A3. The transformed cell cultures were centrifuged, resuspended in 250 ul volumes and plated onto L-agar containing 100 ug/ml ampicillin. The cultures, now on plates, were incubated overnight at 37° C.

C-5. Colonies from the above transformation were picked and plated on LB agar plates containing ampicillin and LB agar plates containing ampicillin and streptomycin.

C-6. Eighteen colones that were ampicillin$^R$ and streptomycin$^S$ were miniprepped as described in section I (B-2) and I (C-3) were found to have the correct sized EcoR I fragment and to be resistant to digestion by Hpa I endonuclease.

C-7. Restriction Gene Clones: The clones identified above as carrying the Hpa I modification methylase were also tested for the Hpa I restriction endonuclease gene. This was performed as described in step I (B-4). Of the eleven looked at, one, p(pBIIHI.2)HpaIRM-7.4-13, was found to produce 155,000 units of Hpa I endonuclease per gram of cells and the other 10 were like p(pBIIHI.2)HpaIRM-7.4-2 and were found to produce 10,000 units of Hpa I endonuclease per gram of cells.

C-8. p(pBIIHI.2)HpaIRM-7.4-13 and p(pBIIHI.2)HpaIRM-7.4-2 were used to transform an isogenic series of *E. coli* strains, looking for potential Mcr A, Mcr B or mrr phenotypes. As described in section II (C-4), both of these RM clones are also unable to transform, and hence be propagated, in any mrr+ strains.

C-9. Hpa I endonuclease was prepared from *E. coli* RRI cells containing p(pBIIHI.2)HpaIRM-7.4-13 as described in section II (C-2). The endonuclease purified was found to have a specific activity of approximately 250,000 units/mg protein.

Table 1

| Amino Acid Sequence to mRNA (DNA) Sequence | | | | | | | | | | |
|---|---|---|---|---|---|---|---|---|---|---|
| 1 letter code | G | A | V | L | I | S | T | D | N | E | Q |
| 3 letter code | Gly | Ala | Val | Leu | Ile | Ser | Thr | Asp | Asn | Glu | Gln |
| mRNA 5' | GGA | GCA | GUA | CUA | AUA | UCA | ACA | GAC | AAC | GAA | CAA |
| | C | C | C | C | C | C | C | U | U | G | G |
| | G | G | G | G | U | G | G | | | | |
| | U | U | U | U | | U | U | | | | |
| | | | | or | | or | | | | | |
| | | | | UUA | | AGC | | | | | |
| | | | | G | | U | | | | | |

| | 1 letter code | K | P | H | R | F | Y | W | C | M | |
|---|---|---|---|---|---|---|---|---|---|---|---|
| | 3 letter code | Lys | Pro | His | Arg | Phe | Tyr | Trp | Cys | Met | |
| | mRNA 5' | AAA | CCA | CAC | CGA | UUC | UAC | UGG | UGC | AUG | 3' |
| | | G | C | U | C | U | U | | U | | |

Table 1-continued

| Amino Acid Sequence to mRNA (DNA) Sequence | |
|---|---|
| G | G |
| U | U |
|  | or |
|  | AGA |
|  | G |

Special Signals
RNA
UAA = Ochre
UAG = Amber
UGA = terminate
Amino Acid Special Symbols
B = D or N
Z = E or Q
Ambigous nucleotide abbreviations
These abbreviations conform to the proposed IUPAC-IUB standard abbreviations.
A C G U/T
U/T = U Uracil/Thymine
G = G Guanine
K = G U
C = C Cytosine
Y = C U Pyrimidine
S = C G
B = C G U
A = A Adenine
W = A U
R = A G Purine
D = A G U
M = A C
H = A C U
V = A C G
N/X = A C G U

What is claimed is:

1. Isolated DNA coding for the HpaI restriction endonuclease, wherein the isolated DNA is obtainable from the vector p(pBIIHI.2KI)HpaIRM10.5-45.

2. A recombinant DNA vector comprising a vector into which a DNA segment coding for the HpaI restriction endonuclease has been inserted.

3. Isolated DNA coding for the HpaI restriction endonuclease and methylase, wherein the isolated DNA is obtainable from the vector p(pBIIHI.2KI)HpaIRM10.5-45.

4. A cloning vector which comprises the isolated DNA of claim 3.

5. The cloning vector of claim 4, wherein the cloning comprises p(pBIIHI.2KI)HpaIRM10.5-45.

6. A host cell transformed by the cloning vector of claim 2, 4 or 5.

7. A method of producing an HpaI restriction endonuclease comprising culturing a host cell transformed with the vector of claim 2, 4 or 5 under conditions suitable for expression of said endonuclease.

* * * * *

UNITED STATES PATENT AND TRADEMARK OFFICE
CERTIFICATE OF CORRECTION

PATENT NO. : 5,298,404
DATED : March 29, 1994
INVENTOR(S) : Benner, et al.

It is certified that error appears in the above-indentified patent and that said Letters Patent is hereby corrected as shown below:

Column 14, line 30, replace "colones" with --colonies--.

Signed and Sealed this

Fourth Day of October, 1994

Attest:

BRUCE LEHMAN

Attesting Officer     Commissioner of Patents and Trademarks